United States Patent [19]

Lé Quan et al.

[11] Patent Number: 4,532,370

[45] Date of Patent: Jul. 30, 1985

[54] PROCESS FOR SYNTHESIZING 1-BUTENE BY DIMERIZATION OF ETHYLENE

[75] Inventors: Nhuong Lé Quan, Aubergenville; Daniel Cruypelinck, Nanteuil-le-Haudouin; Dominique Commereuc, Meudon; Yves Chauvin, Le Pecq; Gérard Leger, Ecully, all of France

[73] Assignee: Institut Francais du Petrole, Rueil-Malmaison, France

[21] Appl. No.: 652,555

[22] Filed: Sep. 20, 1984

[30] Foreign Application Priority Data

Sep. 20, 1983 [FR] France ............................ 83 15040
Sep. 20, 1983 [FR] France ............................ 83 15041

[51] Int. Cl.³ .............................................. C07C 3/21
[52] U.S. Cl. .................................... 585/512; 585/524
[58] Field of Search ...................... 585/510, 512, 524

[56] References Cited

U.S. PATENT DOCUMENTS 3,969,429  7/1976  Belov et al. ................... 585/512
4,101,600  7/1978  Zhukov et al. ................ 585/512

FOREIGN PATENT DOCUMENTS 233558   4/1959   Australia ................... 585/512
7169430  4/1981   Japan ....................... 585/512
856288   12/1960  United Kingdom ............. 585/512
485101   11/1970  U.S.S.R. .................... 585/512
681034   2/1975   U.S.S.R. .................... 585/512
197705   12/1975  U.S.S.R. .................... 585/512

*Primary Examiner*—D. E. Gantz
*Assistant Examiner*—A. Pal
*Attorney, Agent, or Firm*—Millen & White

[57] ABSTRACT

Process for synthesizing 1-butene by dimerization of ethylene, in the presence of a catalyst formed by reacting, in a hydrocarbon medium, a trialkylaluminum with a mixture of an alkyl titanate with an ether. The activity and the selectivity are improved when adding the ether to a pre-formed mixture of alkyl titanate with trialkylaluminum.

10 Claims, No Drawings

PROCESS FOR SYNTHESIZING 1-BUTENE BY DIMERIZATION OF ETHYLENE

The object of the present invention is an improved process for dimerizing elthylene to 1-butene.

BACKGROUND OF THE INVENTION

In the U.S. Pat. No. 2,943,125, K. Ziegler has disclosed a method for dimerizing ethylene to 1-butene by means of a catalyst obtained by admixing a trialkylaluminum compound with a titanium or zirconium tetra-alkoholate; during the reaction, a certain amount of polyethylene of high molecular weight is also formed, which impedes to a large extent the operation. Several improvements have been proposed to reduce the polymer content, particularly in the U.S. Pat. No. 3,686,350 which recommends the use of organic phosphorus compounds jointly with the catalyst elements, in the U.S. Pat. No. 4,101,600 which claims the treatment of the catalyst with hydrogen or in the U.S. Pat. No. 3,879,485 which claims the use of various ethers as solvents for the reaction medium. Although these modifications of the initial catalytic system result in a substantial improvement of the reaction selectivity, they are not of practical use, particularly in an industrial process wherein 1-butene must be separated from the solvent with only traces of polar compounds.

OBJECT OF THE INVENTION

The object of the present invention is to provide a catalyst having exceptional activity and selectivity. This effect is more substantial than that obtained with the coordinates claimed up to now, such as phosphites or amines, and is also more substantial than that obtained with ethers when the latter are in an amount corresponding to a use as solvent, or when they are added to the mixture of hydrocarbylaluminum with alkyl titanate. The process has also the advantage of avoiding the use of said ethers as solvents with the corresponding disadvantages (fractionation difficulties). The process also avoids the use of a solvent of external origin since the constituents of the catalyst may be directly admixed within one of the reaction products or by-products thereof, thus avoiding consumption or recycling of said solvent, which is always difficult to separate from a mixture obtained by oligomerization.

SUMMARY OF THE INVENTION

The invention thus concerns an improved process for converting ethylene to 1-butene, wherein ethylene is contacted with a catalyst obtained by interaction of an alkyl titanate with an alkylaluminum compound, characterized in that said catalyst results from the interaction of a pre-formed mixture of alkyl titanate and ether, in a molar ratio ether/titanate of from 0:5:1 to 10:1, with an aluminum compound of formula $AlR_3$ or $AlR_2H$, wherein R is a hydrocarbyl radical.

The ethers are thus used in a molar ratio from 0.5 to 10, preferably 1 to 3, more particularly 2 moles of ether per mole of titanium compound. Without relying on any theory, it can be deemed that the ether forms a complex with the titanium atom resulting in the hexacoordination that titanium cannot achieve otherwise than by auto-association. When the ether is used in ratios higher than 10, such as 20 or more, or when it is used as solvent for the reaction, it is observed that the reaction is considerably slowed down and that the selectivity is not so good and even, in some cases, the reaction does not occur at all.

The aluminum compounds used to prepare the catalyst comply with the general formulas $AlR_3$ or $AlR_2H$ wherein R is a hydrocarbyl radical, preferably an alkyl radical comprising 2 to 6 carbon atoms, for example triethylaluminum, tripropylaluminum, triisobutylaluminum, diisobutylaluminum hydride or trihexylaluminum.

The ethers, as used according to the invention, may be monoethers or polyethers, for example diethylether, diisopropylether, dibutylether, methyl-tert-butylether, tetrahydrofuran, 1,4-dioxane, dihydropyran, ethylene glycol or dimethylether. Exceptional results are obtained with tetrahydrofuran and/or 1,4-dioxane.

The alkyl titanates, as used according to the invention, comply with the general formula $Ti(OR')_4$ wherein $R'$ is a linear or branched alkyl radical having preferably from 2 to 8 carbon atoms, for example tetraethyl titanate, tetraisopropyl titanate, tetra-n-butyl titanate, tetra-2-ethyl-hexyl titanate. The catalyst components may be contacted within a hydrocarbon and/or within one or more of the oligomerization products, such as hexenes, preferably in the presence of the ethylene. The molar ratio of the aluminum compound to the titanium compound is from about 1:1 to 20:1 and preferably from about 2:1 to 5:1. The titanium concentration in the resultant solution is advantageously from $10^{-4}$ to 0.5 mole per liter and preferably from $2.10^{-3}$ to 0.1 mole per liter.

The catalyst is usually prepared at a temperature from $-10°$ to $+80°$ C., preferably from $-10°$ to $+45°$ C. and, more preferably, from $0°$ to $+40°$ C. Ethylene, when present in the medium, is preferably used in an amount corresponding to the saturation of the solution at the prevailing temperature and at a selected pressure of one atmosphere or more.

The resultant catalyst solution may be used as such or diluted with reaction products. The dimerization of ethylene may be performed at $20°-150°$ C., preferably $20°-70°$ C. and, more preferably, $50°-70°$ C. The pressure is preferably from 0.5 to 8 MPa. In a particular embodiment of the dimerization catalytic reaction, conducted in batch, a selected volume of the catalyst solution, prepared as mentioned above, is introduced into a reactor provided with usual stirring and cooling systems, and subjected therein to an ethylene pressure, preferably from 0.5 to 8 MPa, at a temperature maintained between $20°$ and $70°$ C., preferably between $50°$ and $70°$ C. The reactor is fed with ethylene at constant pressure until the total volume of liquid produced amounts to 2 to 50 times the volume of the initially introduced catalytic solution; the catalyst is then destroyed, for example by adding water, and the reaction products and the optional solvent are withdrawn and separated.

When proceeding continuously, the operation is preferably as follows: the catalytic solution is introduced with ethylene into a reactor stirred by conventional means or by external recirculation. The temperature is maintained between about $20°$ C. and $70°$ C., preferably between $50°$ C. and $70°$ C., and the pressure is preferably from 0.5 to 8 MPa. Through an expansion valve which maintains a constant pressure, a portion of the reaction mixture is discharged at a rate by weight equal to the feeding rate by weight of the supplied fluids. The soexpanded fluid is fed to a distillation column system for separating, on the one hand, 1-butene from ethylene which is fed back to the reactor and, on the other hand, hexenes and octenes, a portion of which is fed back to the catalyst preparation section. The column bottoms containing the catalyst and heavy products may be burnt, or the recovered catalyst may be recycled.

In a preferred embodiment, the catalyst components are admixed in ethylene atmosphere at a temperature from −10° to +45° C., then the temperature is increased up to 50°–70° C. and the dimerization reaction is allowed to continue. In a still more at a temperature from −10 to +° 45° C. for 30 seconds to 24 hours before increasing the temperature up to 50°–70° C.

EXAMPLES

The following examples illustrate the invention without however limiting the scope thereof.

EXAMPLE 1

A stainless steel autoclave of the Grignard type, of 250 ml capacity, provided with a double jacket, whereby the temperature may be adjusted to 18° C. by water circulation, is fed under ethylene atmosphere successively with: 2.5 ml of a triethyl aluminum solution in a cut of hexenes prepared by admixing 0.25 ml of triethylaluminum with 9.75 ml of hexenes, then with a solution of a tetra-n-butyl titanate-tetrahydrofuran complex prepared by admixing 0.05 ml of tetra-n-butyl titanate with 0.024 ml of tetrahydrofuran and 2.42 ml of hexenes cut. The molar ratio of the tetrahydrofuran to the titanate is 2.1:1. After 2 minutes of interaction, the temperature is raised to 55° C. and the ethylene pressure to 2 MPa.

After 2h30 of reaction, the ethylene feed is discontinued and the catalyst is destroyed by injecting 2 ml of water under pressure. 133 g of ethylene as a total were consumed.

In addition to the unreacted ethylene, 0.28 g of n-butane, 92.40 g of 1-butene, 6.46 g of hexenes, 0.17 g of octenes and 0.0027 g of polyethylene are recovered. The analysis of the $C_4$ fraction by gas phase chromatography with a flame ionization detector shows a total 2-butene content lower than 10 ppm. Polyethylene amounts to 27 ppm.

In these conditions, the catalyst productivity is increased to 13,088 g of 1-butene per gram of titanium metal.

EXAMPLE 2 (comparison, forming no part of the invention)

In the same apparatus as used in example 1, and everything else being unchanged, the amount of supplied tetrahydrofuran is increased so as to obtain a molar ratio of tetrahydrofuran to titanate of 20:1 instead of 2.1:1. After 5 h at 55° C., no ethylene conversion is observed.

EXAMPLE 3 (forming no part of the invention)

In this example, the apparatus and the operating conditions are the same as in example 1 except that the amount of titanium compound is doubled, the amount of aluminum compound is doubled and no tetrahydrofuran is used. 91.6 g of 1-butene, 0.28 g of butane, 11.8 g of hexenes, 0.68 g of octenes and 0.1 g of polyethylene are obtained. Resultant 1-butene contains 360 ppm of 2-butene. The catalyst productivity is only 6,500 g of butene per g of titanium metal.

EXAMPLE 4 (forming no part of the invention)

In successive order, 2.5 ml of a triethylaluminum solution in a cut of hexenes prepared by admixing 0.25 ml of triethylaluminum with 9.75 ml of hexenes, then 0.024 ml of tetrahydrofuran and finally a solution of 0.05 ml of tetra-n-butyl titanate in 2.42 ml of hexenes cut are introduced into the same apparatus as used in example 1, under ethylene atmosphere. The reaction is then conducted under the same conditions and the same procedure as in example 1. The catalyst productivity is only 5,592 g of 1-butene per g of titanium metal. Polyethylene amounts to 70 ppm.

EXAMPLE 5 (forming no part of the invention)

Under ethylene atmosphere, 2.5 ml of a triethylaluminum solution in a cut of hexenes, prepared by admixing 0.25 ml of triethylaluminum with 9.75 ml of hexenes, then a solution of 0.05 ml of tetra-n-butyl titanate in 2.42 ml of hexenes cut, and finally 0.024 ml of tetrahydrofuran are successively introduced in said order into the same apparatus as in example 1. The reaction is performed under the same conditions and with the same procedure as in example 1.

The catalyst productivity is only 9,231 g of 1-butene per g of titanium metal. Polyethylene amounts to 42 ppm.

EXAMPLE 6

2.5 ml of a triethylaluminum solution in a cut of hexenes, prepared by admixing 0.25 ml of triethylaluminum with 9.75 ml of hexenes, then a solution of a tetra-n-butyl titanate 1.4-dioxane complex, prepared by admixing 0.05 ml of tetra-n-butyl titanate with 0.025 ml of 1,4-dioxane and 2.42 ml of hexenes cut (the molar ratio of 1,4-dioxane to titanate being 2.07:1), are introduced into the same apparatus as in example 1, under ethylene atmosphere, while maintaining the temperature at 18° C. After 2 minutes of interaction, the temperature is brought to 55° C. and the ethylene pressure to 2 MPa.

After 2 h 30, the reaction is discontinued by introduction of 2 ml of water under pressure. 120 g of ethylene are consumed as a whole. 0.18 g of n-butane, 87.09 g of 1-butene, 6.88 g of hexenes, 0.20 g of octenes and 0.0042 g of polyethylene are recovered in addition to the unreacted ethylene.

The $C_4$ fraction comprises 2060 ppm of butane and a total 2-butene amount lower than 10 ppm. Polyethylene amounts to 45 ppm. The catalyst productivity reaches 12,336 g of 1-butene per gram of titanium metal.

EXAMPLE 7

1.25 ml of a triethylaluminum solution in a cut of hexenes, prepared by admixing 0.5 ml of triethylaluminum with 9.5 ml of hexenes, than a solution of a n-butyl titanate-glyme complex (glyme is ethyleneglycol dimethyl ether), prepared by admixing 0.05 ml of n-butyl titanate with 0.05 ml glyme and 2.5 ml of hexenes cut (the molar ratio of glyme to titanate being 3.2:1) are introduced into the same apparatus as in example 1, under ethylene atmosphere, while maintaining the temperature at 18° C.

After 2 minutes of interaction, the temperature is brought to 55° C. and the ethylene pressure to 2 MPa.

After 2 hours of reaction, the catalyst is destroyed by addition of 2 ml of water under pressure. 136 g of ethylene are consumed as a total.

0.22 g of n-butane, 89.28 g of 1-butene, 9.83 g of hexenes, 0.41 g of octenes and 0.0139 g of polyethylene are recovered in addition to the unreacted ethylene. The $C_4$ fraction comprises 2400 ppm of n-butane and the total 2-butene content is lower than 10 ppm. Polyethylene amounts to 139 ppm. The catalyst productivity reaches 12,646 g of 1-butene per gram of titanium metal.

EXAMPLE 8 (comparison, forming no part of the invention)

Example 5 is repeated except that the glyme amount is increased so as to obtain a molar ratio of glyme to titanate of 230:1 instead of 3.2:1.

The catalyst productivity is then only 1,350 g of 1-butene per gram of titanium metal.

EXAMPLE 9

2.5 ml of a triethylaluminum solution in a cut of hexenes, prepared by admixing 0.5 ml of triethylaluminum with 19.5 ml of hexenes, then 2.5 ml of a solution of a n-butyl titanatedihydropyran complex, prepared by admixing 0.4 ml of n-butyl titanate with 0.215 ml of dihydropyran in 19.6 ml of hexenes, the molar ratio of dihydropyran to titanate being 2:1, are introduced, under ethylene atmosphere, into the same apparatus as in example 1, while maintaining the temperature at 18° C. After 2 minutes of interaction, the temperature is brought to 55° C. and the ethylene pressure to 2 MPa.

The catalyst is destroyed after 1 h 30 of reaction. The recovered products indicate a catalyst productivity of 6,146 g of 1-butene per gram of titanium metal.

EXAMPLE 10

2.5 ml of a triethylaluminum solution in heptane, prepared by admixing 0.5 ml of triethylaluminum with 19.5 ml of heptane, then 2.5 ml of a solution of an isopropyl titanate 1,4-dioxane complex, prepared by admixing 0.34 ml of isopropyl titanate with 0.2 ml of 1,4 dioxane in 19.4 ml of heptane, the molar ratio of the dioxane to the titanate being 2:1, are introduced, under ethylene atmosphere, into the same apparatus as in example 1, while maintaining the temperature at 35° C. After 5 minutes of interaction, the temperature is brought to 70° C. and the ethylene pressure to 3 MPa. The catalyst is destroyed after 2 hours of reaction.

The catalyst productivity is 8,500 grams of 1-butene per gram of titanium metal.

What is claimed as the invention is:

1. An improved process for converting ethylene to 1-butene wherein ethylene is contacted with a catalyst obtained by reacting an alkyl titanate with an alkylaluminum compound, characterized in that said catalyst results from reacting a preformed mixture of alkyl titanate and ether, in a molar ratio ether/titanate from 0.5:1 to 10:1, with an aluminum compound of formula $AlR_3$ or $AlR_2H$, wherein each R is a hydrocarbyl radical.

2. A process according to claim 1, wherein the molar ratio of the ether to the alkyl titanate is from about 1:1 to 3:1.

3. A process according to claim 1, wherein said reaction is performed in a solvent consisting of hexenes recovered as by-products of the reaction.

4. A process according to claim 1, wherein the ether is diethylether, isopropylether, dibutylether, methyl-tert-butylether, tetrahydrofuran, 1,4-dioxane, dihydropyran or ethyleneglycol dimethylether.

5. A process according to claim 4, wherein the ether is 1,4-dioxane.

6. A process according to claim 4, wherein the ether is tetrahydrofuran.

7. A process according to claim 1, wherein the reaction of the preformed mixture of alkyl titanate and ether with the aluminum compound is performed at a temperature from $-10°$ to $+45°$ C. in ethylene atmosphere and the temperature is then increased to 50°–70° C. to convert ethylene to 1-butene.

8. A process according to claim 7, wherein the admixed catalyst components are maintained at a temperature from $-10°$ to $+45°$ C. for 30 seconds to 24 hours before increasing the temperature to 50°–70° C.

9. A process according to claim 1, wherein the molar ratio of the aluminum compound to the titanium compound is from 1:1 to 20:1 and the titanium concentration is from $10^{-4}$ to 0.5 mole per liter when the catalyst is used for converting ethylene to 1-butene at a temperature from 20° to 150° C. under a pressure from 0.5 to 8 MPa.

10. A process according to claim 9 wherein the temperature is from 20° to 70° C.

* * * * *